United States Patent [19]

Shapiro

[11] Patent Number: 4,538,602

[45] Date of Patent: Sep. 3, 1985

[54] LEG WRAP

[76] Inventor: Theodore Shapiro, One Bridle La., Sands Point, N.Y. 11050

[21] Appl. No.: 568,385

[22] Filed: Jan. 5, 1984

[51] Int. Cl.$^3$ .............................................. A61F 13/00

[52] U.S. Cl. ..................................................... 128/132

[58] Field of Search .................... 128/82, 83, 132, 149, 128/153, 157, 165, 166, 161

[56] References Cited

U.S. PATENT DOCUMENTS

| | | | |
|---|---|---|---|
| 978,794 | 12/1910 | Van Gorder | 128/169 |
| 3,338,028 | 10/1967 | Freemann | 128/165 |
| 3,504,672 | 4/1970 | Moon | 128/169 |
| 3,536,068 | 10/1970 | Stubbs | 128/169 |
| 3,667,462 | 6/1972 | Moon | 128/169 |
| 3,880,161 | 4/1975 | Fossel | 128/169 |

*Primary Examiner*—C. Fred Rosenbaum
*Assistant Examiner*—Christa K. Scott
*Attorney, Agent, or Firm*—Lackenbach, Siegel, Marzullo, Presta & Aronson

[57] ABSTRACT

An animal leg wrap having both an inner and an outer layer are disclosed. The outer end of the inner layer is connected to the inner end of the outer layer. The inner layer is wrapped several times around the leg of the animal and when the outer end of the inner layer is wrapped, the wrapping of the outer layer begins. When the outer end of the outer layer is wrapped, the wrap is fastened.

5 Claims, 7 Drawing Figures

LEG WRAP

FIELD OF THE INVENTION

This invention relates to a leg wrap which can be used to protect the legs of four-legged animals, such as horses.

BACKGROUND OF THE INVENTION

In certain situations, it is common to wrap the lower legs of a horse near the hoof area. Such situations include, for example, periods after the horse has been strenuously exercised and periods of shipping during which the horse will be standing in a moving vehicle for an extended period of time.

This type of wrapping provides protection in several ways. Firstly, it provides support for the lower leg or ankle area and prevents the area from swelling. Secondly, it protects the lower leg or ankle area from superficial cuts and bruises, as may be especially likely to occur in a shipping situation.

In order to provide the aforementioned advanages, it is important to wrap the area tightly so as to provide support, but not so tightly so as to cut off circulation to the area. Most of the prior art devices which are available have an inner layer and an outer layer wherein the inner layer and the outer layer are connected to each other along the top and bottom edges of both layers. Usually the inner layer is a cushioning layer and the outer layer is a protective layer. This type of wrap is applied by wrapping it around the leg one complete time and then closing the wrap. Such wraps are disclosed, for example, in U.S. Pat. Nos. 1,945,266; 2,194,921; 4,099,269; and 4,342,185. These wraps have the disadvantage that, while they are generally adequate as protective devices, they are generally inadequate as means for providing support for the leg.

OBJECT OF THE INVENTION

It is, therefore, an object of the present invention to provide a leg wrap which is useful for providing protection to the lower leg or ankle area of a four-legged animal, as well as for providing support for the lower leg or ankle area of such an animal.

SUMMARY OF THE INVENTION

The present invention is an animal leg wrap having both an inner layer and an outer layer. The outer end of the inner layer is connected to the inner end of the outer layer. The inner layer is then wrapped several times around the leg of the horse and when the outer end of the inner layer is reached, the wrapping of the outer layer begins. When the outer end of the outer layer is reached, the wrap is fastened.

The invention can be better understood in connection with the accompanying drawings.

DETAILED DESCRIPTION OF THE INVENTION

Figure 1:
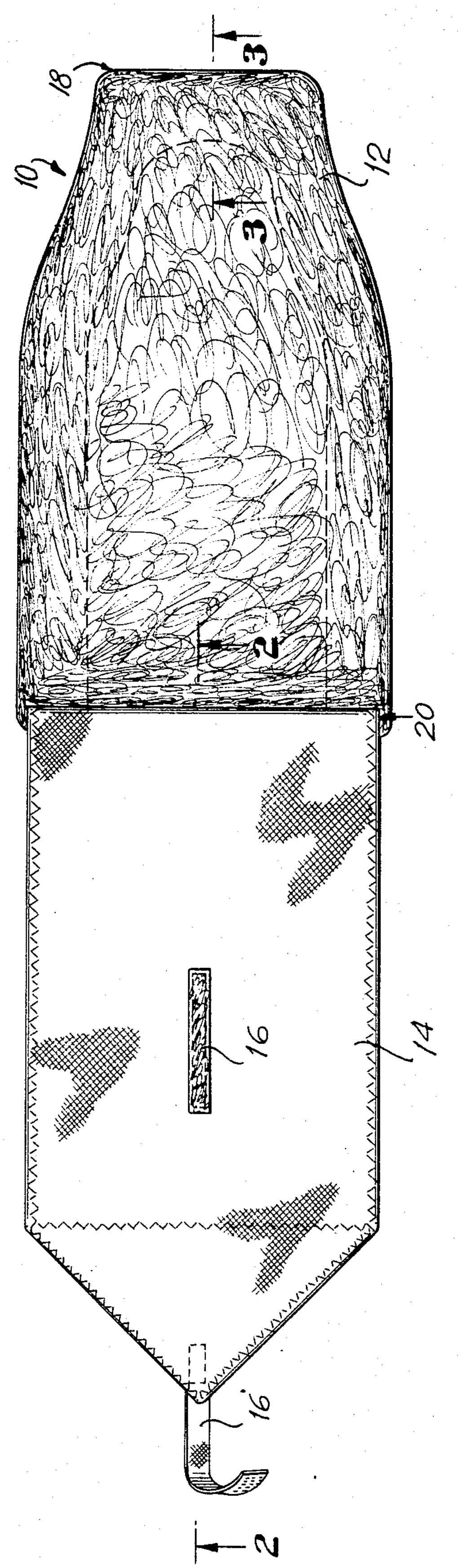
FIG. 1 is a plan view of an embodiment of the invention.
Figure 2:
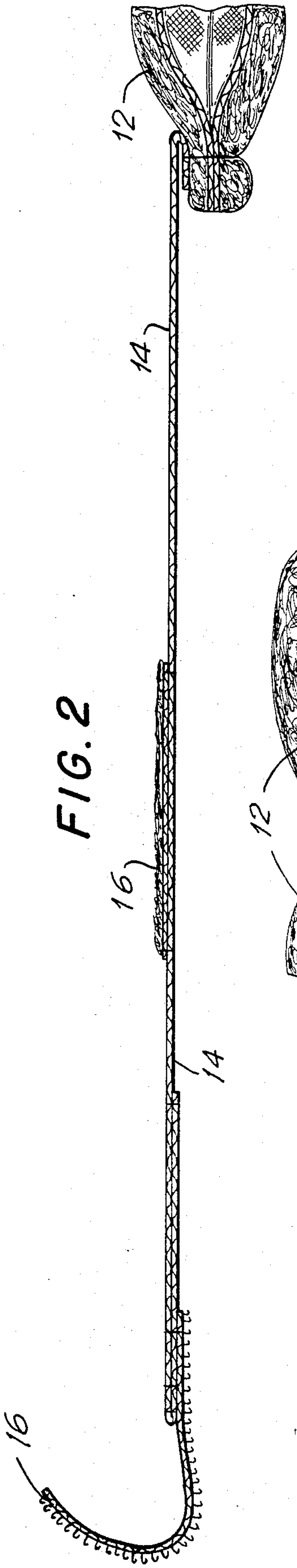
FIG. 2 is a cross-sectional view taken along section line 2—2 of FIG. 1.
Figure 3:
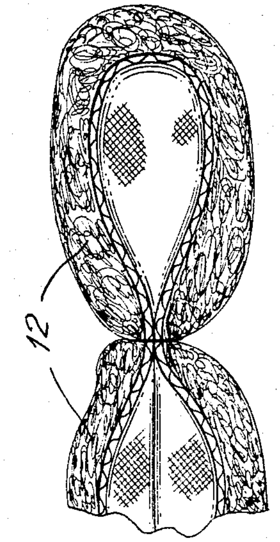
FIG. 3 is a cross-sectional view taken along section line 3—3 of FIG. 1.
Figure 5:
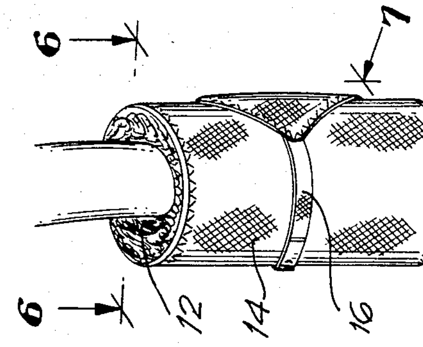
FIG. 5 is a perspective view showing the invention as it would be while in use on a horse.

The invention is a leg wrap 10 having an inner layer 12 and an outer layer 14. The outer end of the inner layer 12 is joined to the inner end of the outer layer 14 at juncture 20 between the inner and outer layers. The leg wrap 10 also comprises fastening means 16 on outer layer 14 for holding leg wrap 10 in position when it is wrapped in overlapping relation around the leg of an animal.

The inner layer 12 is constructed of any suitable natural or synthetic material. The material should be relatively thick, i.e., from about $\frac{1}{8}$ to about $\frac{3}{8}$ inches thick, cushiony, flexible, and air permeable so as to allow the animal's skin to breath. Suitable materials include, but are not limited to, sheepskin, wool, flannel, foam, and combinations of the above.

The inner layer 12 preferably is substantially hexagonal in shape. It is tapered toward the inner end 18 of the layer 12. This is considered to be an important feature of the invention as it allows the wrap to be wrapped lower on the leg than is ordinarily possible.

Outer layer 14 is constructed of a suitable lightweight protective material. The material may be stretchable at least in the longitudinal or horizontal direction. In a preferred embodiment, it is stretchable also in both diagonal directions, but not in the lateral or vertical direction. Any edge finishing which must be done on outer layer 14 should be done using a zigzag stitch so as to retain the stretchability of the material.

The outer end of inner layer 12 is joined to the inner end of outer layer 14 at juncture 20. In a preferred embodiment, this juncture is a seam running along the entire length of the adjacent ends of inner layer 12 and outer layer 14. In an alternative embodiment, the outer end of inner layer 12 is removably attached to the inner end of outer layer 14 at juncture 20, for example, by snaps or other similar types of fastening means.

Fastening means 16 are secured to outer layer 14 in any suitable manner. One end of the fastening means is secured to an outer end of the outer layer while the other end of the fastening means 16 is secured to the outside of outer layer 14 in the center portion of outer layer 14. In a preferred embodiment, Velcro fastening means are used, but other types of fastening means, such as, for example, snaps or hooks and eyes, can also be used.

In use, leg wrap 10 is secured to the leg of a horse by holding the inner end 18 of inner layer 12 to the horse's leg near the ankle joint. Because inner layer 12 is tapered toward its inner end 18 the wrap 10 can be secured lower on the horse's leg than is ordinarily possible. The placement of the wrap on the animal is low enough to allow the outer layer 14 of the wrap 10 to extend over the animal's hoof without restricting leg movement at the ankle joint.

Figure 4:
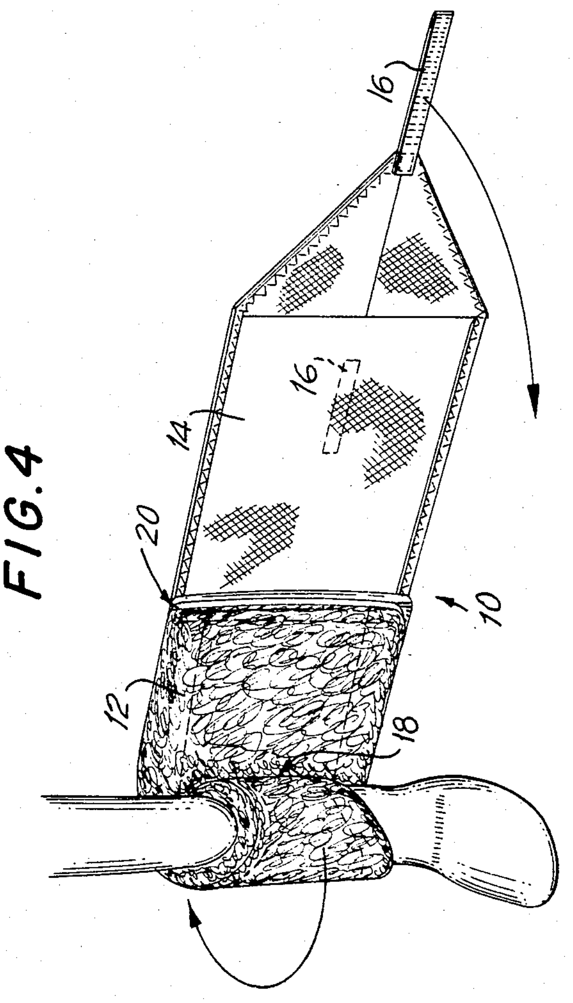
FIG. 4 is a perspective view of the invention shown in the position it would be in while being put on a horse.
Figure 7:
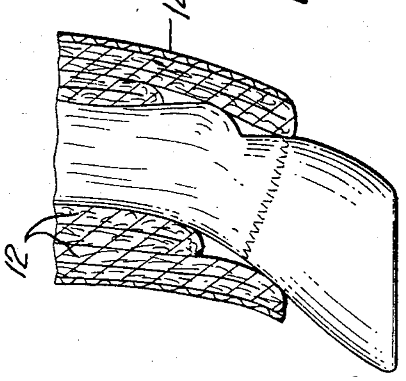
FIG. 7 is a cross-sectional view taken along section line 7—7 of FIG. 5.
Figure 6:
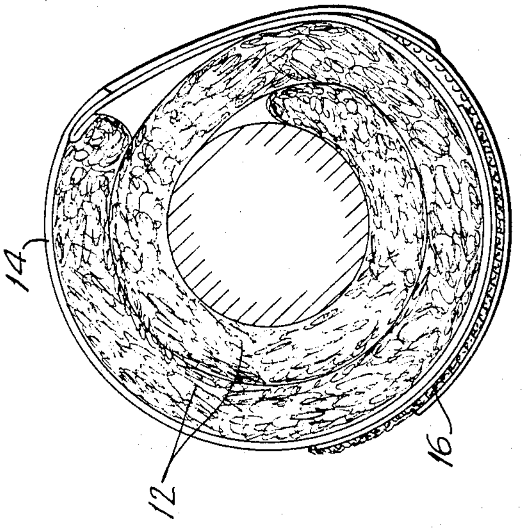
FIG. 6 is a cross-sectional view taken along section line 6—6 of FIG. 5.

Once the inner end 18 of inner layer 12 is in place against the horse's leg, the wrap 10 is wrapped around, as shown in FIG. 4, until the outer end of outer layer 14 is reached. When wrap 10 is completely wrapped, it may be secured to itself by means of fastening means 16.

Although the present invention has been described in some detail by way of illustration and example for purposes of clarity of understanding, it will, of course, be understood that various changes and modifications may be made in the form, details, and arrangements of the parts without departing from the scope of the invention as set forth in the appended claims.

What is claimed is:

1. A leg wrap for a four-legged animal comprising:
an inner layer having an outer end and being of a length sufficient to be wrapped a plurality of times around the leg of the animal; an outer layer having an inner end secured to the outer end of said inner layer; and,
fastening means attached to said outer layer for holding the wrap closed when said inner and outer layers are wrapped in overlapping relation around the leg of the animal;

said inner layer being tapered toward its inner end so that said outer layer covers the hoof of the animal without restricting leg movement at the ankle joint when said inner and outer layers are wrapped in overlapping relation around the leg of the animal.

2. A leg wrap as defined in claim 1 wherein said inner layer is constructed of a material which is cushiony, flexible and air-permeable.

3. A leg wrap as defined in claim 1 wherein said inner layer is tapered toward its inner end so that the outer layer covers the hoof of the animal without restricting leg movement at the ankle joint when said inner and outer layers are wrapped in overlapping relation around the leg of the animal.

4. A leg wrap as defined in claim 1 wherein said outer layer is a stretchable protective layer.

5. A leg wrap as defined in claim 1 wherein said fastening means comprise Velcro fastening means.

* * * * *